United States Patent [19]

Shamshoum et al.

[11] Patent Number: 5,227,558
[45] Date of Patent: Jul. 13, 1993

[54] AROMATIC ALKYLATION PROCESS EMPLOYING STEAM MODIFIED ZEOLITE BETA CATALYST

[75] Inventors: Edwar S. Shamshoum, Houston;
Thomas R. Schuler, Galena Park;
Ashim K. Ghosh, Houston, all of Tex.

[73] Assignee: Fina Technology, Inc., Dallas, Tex.

[21] Appl. No.: 833,244

[22] Filed: Feb. 10, 1992

[51] Int. Cl.$^5$ .............................................. C07C 2/64
[52] U.S. Cl. .................................................. 585/446
[58] Field of Search ........................................ 585/446

[56] References Cited
U.S. PATENT DOCUMENTS

| | | | |
|---|---|---|---|
| 4,950,823 | 8/1990 | Harandi et al. | 585/446 |
| 5,051,164 | 9/1991 | Herbst et al. | 502/64 |
| 5,164,169 | 11/1992 | Rubin | 423/709 |
| 5,164,170 | 11/1992 | Rubin | 423/709 |

Primary Examiner—W. J. Shine
Assistant Examiner—C. Everhart
Attorney, Agent, or Firm—Joe A. Schaper; John K. Abokhair; M. Norwood Cheairs

[57] ABSTRACT

A process for the alkylation of aromatic compounds by low molecular weight alkylating agents is provided. The process includes the use of a steam modified zeolite beta alkylation catalyst. Such steam modification of the beta zeolite is achieved by steaming the catalyst at a temperature of between about 550° and 750° C., thereby dealuminating the zeolite to obtain a silica to alumina mole ratio of between about 50 and 350. Either liquid or vapor phase alkylation conditions may be utilized, or intermediate conditions in which liquid and vapor phases exist. The process is particularly useful the vapor phase ethylation of benzene to produce ethylbenzene with little or no xylene make.

14 Claims, 1 Drawing Sheet

AROMATIC ALKYLATION PROCESS EMPLOYING STEAM MODIFIED ZEOLITE BETA CATALYST

TECHNICAL FIELD OF THE INVENTION

This invention relates to a process for the alkylation of aromatic compounds by low molecular weight alkylating agents over a steam modified zeolite beta catalyst. Vapor phase alkylation conditions are preferred, but the process also may be carried out in the liquid phase or under intermediate conditions in which both liquid and vapor phases exist.

BACKGROUND OF THE INVENTION

Processes for the alkylation of aromatic feedstocks and the use of molecular sieves as catalysts in such alkylation processes are well known in the art. Such alkylation processes may be used to produce mono- or polyalkylated products ranging from low to high molecular weights and may be carried out in the vapor phase, in the liquid phase, or under intermediate conditions in which both liquid and vapor phases exist.

U.S. Pat. No. 4,301,316 to Young discloses the use of a crystalline zeolite alkylation catalyst in the alkylation of benzene by relatively long chain length alkylating agents having one or more reactive alkyl groups of at least five carbon atoms. The reactants may be in either the vapor phase or the liquid phase, and the zeolite catalyst may be either modified or unmodified. Preferred zeolite catalyst include zeolite beta, ZSM-4, ZSM-20, ZSM-38, and synthetic and naturally occurring isotopes thereof, such as zeolite omega and others. The zeolites may be subjected to various chemical treatments, and may also be subjected to thermal treatment, including steam or calcination in air, hydrogen and an inert gas. Specifically disclosed in Young is the reaction of benzene and 1-dodecene over zeolite beta in a flow reactor at 250° C. and 600 psig.

U.S. Pat. No. 4,185,040 to Ward et. al. discloses an alkylation process employing a molecular sieve catalyst of low sodium content which is said to be especially useful in the production of ethylbenzene from benzene and ethylene, and cumene from benzene and propylene. The Na$_2$O content of the zeolite should be less than 0.7 weight percent and preferably less than 0.5 weight percent. Examples of suitable zeolites include molecular sieves of the X, Y, L, B, ZSM-5, and Omega crystal types, with steam stabilized hydrogen Y zeolite being preferred. The alkylation process is preferably carried out under conditions in which at least some liquid phase is present, at least until substantially all of the olefin alkylating agent is consumed.

Another alkylation procedure is disclosed in U.S. Pat. Nos. 4,798,816 and 4,876,408 to Ratcliffe et. al. Ratcliffe et. al. employ molecular sieve alkylation catalyst which have been treated in a manner to improve selectivity to monoalkylation, specifically to the propylation of benzene to produce cumene. Selectivity is said to be increased by at least one percentage point by first depositing a carbonaceous material on the catalyst and then subjecting the resultant carbon containing catalyst particles to combustion. Specifically disclosed zeolitic crystalline molecular sieves include those selected from the group of Y zeolites, fluorided Y zeolites, X zeolites, zeolite beta, zeolite L and zeolite omega. The zeolites may be modified to arrive at products of reduced alumina content and reduced sodium content.

Aromatic alkylation reactions such as the alkylation of benzene with ethylene are highly exothermic reactions. As a result the alkylation reactions may be carried out in stages with intermediate cooling steps. For example, U.S. Pat. No. 4,107,224 to Dwyer discloses the vapor phase ethylation of benzene over a zeolite catalyst in a down flow reactor with the intermediate injection of cold reactants in a diluent. Specifically disclosed is the interstage injection of ethylene and benzene. Dwyer characterizes the catalyst suitable for use in his invention in terms of those having a constraint index within the approximate range of one to twelve. Suitable zeolites, with the constraint index in parenthesis, are ZSM-5 (8.3), ZSM-11 (8.7), ZSM-12 (2), ZSM-35 (4.5), ZSM-38 (2) and similar materials. Various molecular sieves including, inter alia, zeolite beta (constraint index 0.6), are disclosed as having constraint indices outside of the range suitable for the Dwyer ethylbenzene production process.

U.S Pat. No. 4,891,458 to Innes is directed to a process for the alkylation or transalkylation of an aromatic hydrocarbon with a $C_2$ to $C_4$ olefin alkylating agent under at least partial liquid phase conditions utilizing zeolite beta as the catalyst.

SUMMARY OF THE INVENTION

In accordance with the present invention, there is provided a new and advantageous process for the alkylation of aromatic substrates by relatively low molecular weight alkylating agents. The process employs a zeolite beta catalyst which has been steam modified prior to use. Such steam modification results in dealumination of the zeolite, and is achieved by repeated ammonium exchanges and calcination of the parent or "as synthesized" zeolite, followed by steam treatment and additional ammonium exchanges under acidic conditions. After modification, the beta zeolite preferably has a silica to alumina mole ratio ($SiO_2/Al_2O_3$) between about 50 and 350. Under vapor phase conditions, the modified beta catalyst exhibits stability and selectivity toward desired products similar to that of an unmodified beta catalyst, but with a reduction in the production of undesirable products. Although vapor phase alkylation conditions are preferred, the catalyst may also be employed in liquid phase operations, or intermediate conditions in which both liquid and vapor phases exist.

In carrying out the process of the present invention, a feedstock containing an aromatic substrate is supplied to a reaction zone and brought into contact with the steam modified zeolite beta catalyst. A $C_2$ to $C_4$ alkylating agent is also supplied to the reaction zone which is preferably operated under such temperature and pressure to maintain essentially vapor phase conditions, while causing alkylation of the aromatic substrate in the presence of the modified beta catalyst. The resulting alkylated aromatic compound is then recovered from the reaction zone. The present vapor phase alkylation process is characterized by excellent alkylating agent conversions, high selectivity toward mono-alkylation and low selectivity toward unwanted products.

A preferred application of the present invention is in the vapor phase alkylation of benzene with ethylene to produce ethylbenzene. The process is preferably carried out under alkylation conditions which result in extremely low, or no, xylene make, based upon the amount of ethylbenzene produced.

In a most preferred embodiment of the present invention, the alkylating agent is diluted with a diluting agent prior to being supplied to the reaction zone. Suitable diluting agents are generally inert, or nonreactive, gases, with nitrogen being most preferred. Although varying amounts of dilution may be used, it is preferred that the concentration of the inert, or non-reactive, gas be greater than the concentration of the alkylating agent in the diluted feedstream, with 70% inert gas and 30% alkylating agent being most preferred. Additional details regarding the use of such diluted alkylating agent feedstreams are disclosed in co-pending application Ser. Nos. 766,887 and 766,888, (both filed Sep. 27, 1991), the disclosures of which are incorporated herein by reference.

DETAILED DESCRIPTION

Figure 1:
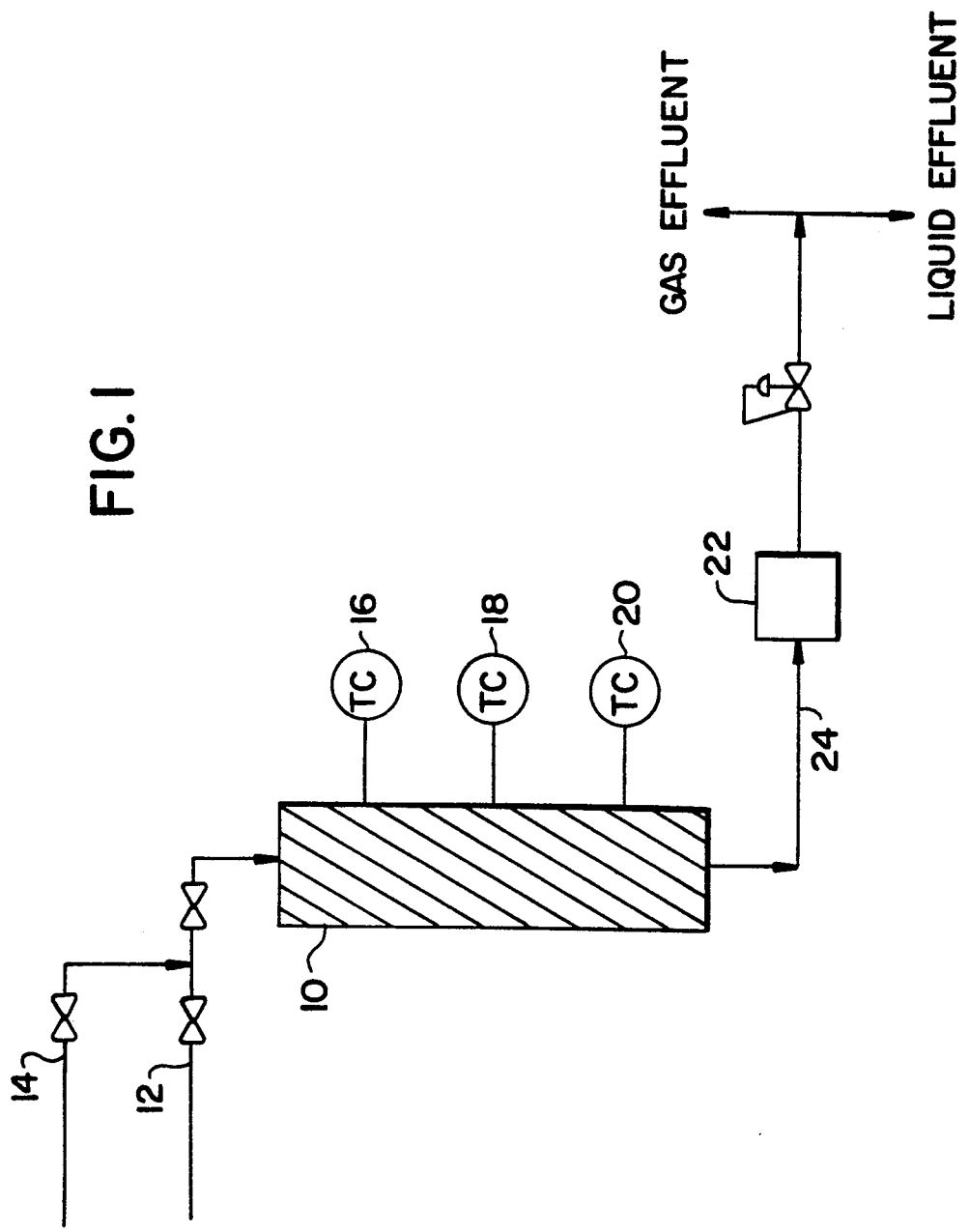
FIG. 1 is a schematic illustration of a specific embodiment for carrying out the present invention.

The present invention relates to an improved aromatic alkylation process which employs a steam modified, dealuminated zeolite beta catalyst. Vapor phase alkylation conditions are preferred, but liquid or intermediate conditions (wherein both liquid and vapor phases exist) may be utilized. The process is particularly applicable to the ethylation of benzene, producing little or no xylene make, and at times the invention will be described specifically by reference to the production of ethylbenzene. The present invention, however, may also be utilized to produce other alkylaromatic products. For example, the invention may be applied to the reaction to propylene with benzene to produce cumene. Additionally, while olefinic alkylating agents normally will be employed, other alkylating agents, such as alkynes, alkylhalides, alcohols, ethers, and esters, as disclosed, for example in U.S. Pat. No. 3,551,510 to Pollitzer et. al. may be used. Further, other aromatic substrates, such as toluene and xylene, also may be subjected to alkylation in accordance with the present invention.

As noted above, the zeolite beta catalyst employed in the present invention is dealuminated by steam treatment prior to use. Such a modified beta zeolite is preferably prepared by first ion-exchanging a parent, or "as synthesized", beta zeolite with ammonium ions, calcining the ammonium exchanged zeolite, dealuminating the calcined zeolite by steam treatment, and then subjecting the dealuminated zeolite to two successive ammonium ion-exchanges under acidic conditions. The dealuminated beta zeolite is then extruded with a binder and calcined to convert the catalyst to its active hydrogen form.

Basic procedures for the preparation of the parent or "as synthesized" crystalline zeolite beta are disclosed in U.S. Pat. Nos. 3,308,069 (Wadlinger et. al.) and 4,642,226 (Calvert et. al.) and European Patent Application Nos. 159,846 (Reuben); 165,208 (Bruce et. al.); 186,447 (Kennedy et. al.), the entire disclosures of which are incorporated herein by reference. Preferably, the parent zeolite beta will have a low sodium content, i.e. less than 0.05 wt. % expressed as $Na_2O$, with a sodium content of less than 0.02 wt. % being most preferred.

As disclosed in the above-referenced U.S. patents to Wadlinger et. al., and Calvert et. al., the parent zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. The parent zeolite beta is characterized by a silica to alumina molar ratio (expressed as $SiO_2/Al_2O_3$) of between about 20 and 50.

The parent zeolite beta is then subjected to ion-exchange with ammonium ions (at uncontrolled pH). It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours. The calcined zeolite is then dealuminated by steaming at a temperature between about 550° C. and 750° C. for approximately two hours. The dealuminated zeolite is then subjected to two successive ammonium ion-exchanges under acid conditions resulting in proton ion exchange. The modified beta zeolite preferably will have a silica to alumina ratio ($SiO_2/Al_2O_3$) between about 50 and 350 most preferably between about 70 and 200.

After the final ammonium ion-exchange, the beta zeolite is mixed with a binder, such as alumina sol, gamma-alumina or other refractory oxides to produce a mulled zeolite-binder mixture containing about 20% binder. This mixture is then pelletized by any suitable technique, such as extrusion, and the resulting pellets dried. The pelletized binder-beta zeolite product is then calcined under conditions sufficient to place the zeolite in its active hydrogen beta form. Calcination at a temperature of approximately 530° C. for two to four hours is preferred.

In accordance with the process of the present invention, an aromatic feedstock is supplied to a reaction zone where it is brought into contact with a steam modified beta zeolite catalyst having a silica to alumina ratio ($SiO_2/Al_2O_3$) between about 50 and 350. A $C_2$ to $C_4$ alkylating agent is also supplied to the reaction zone, which is preferably operated at such temperature and pressure to maintain essentially vapor phase conditions. For the production of ethylbenzene, such temperature and pressure conditions fall within the range of between about 270° and 400° C. and 200 and 600 psig, respectively, with a temperature and pressure of about 300° C. and 300 psig, respectively, being preferred. Further, it is preferred that the gas phase alkylation be carried out in a reactor operated in a down-flow mode.

When essentially liquid phase conditions are desired, the reaction temperature may range from about 38° C. to 300° C., and is preferably between about 120° C. and 260° C. For the liquid phase ethylation of benzene, a reaction temperature between about 190° C. and 240° C. is preferred. Further, when operating under essentially liquid phase conditions, it is preferred that an up-flow reactor mode be employed.

Additional reaction conditions for gas or liquid phase operations include a liquid hourly space velocity (LHSV) between about 1 and 100 $hr^{-1}$ and an aromatic substrate:alkylating agent molar ratio between about 1 and 50. LHSV's between about 10 and 70 hr$^{-1}$ and aromatic substrate:alkylating agent molar ratios between about 7 and 12 are preferred. After alkylation of the aromatic substrate has occurred in the presence of the steam modified beta zeolite, the alkylated aromatic product is recovered from the reaction zone.

As noted above, it is preferred to utilize a diluted alkylating agent feedstream in the process of the present invention. Suitable diluting agents generally include gases which are not deleterious to the alkylation reaction or catalyst, such as, for example, methane, $C_2$ to $C_4$ paraffins, and inert, or other non-reactive, gases. A particularly preferred diluting agent is nitrogen utilized in an amount such that the diluted alkylating agent feedstream consists of approximately 30 mole percent alkylating agent and 70 mole percent nitrogen.

With reference to the drawings, a schematic diagram of a specific embodiment for carrying out the process of the present invention is shown in FIG. 1. Feedstreams 12 and 14 provide the aromatic substrate and alkylating agent, respectively, to reactor 10. The reactor 10 includes a catalyst bed containing the steam modified beta zeolite. Thermocouples 16, 18, and 20 are preferably provided for monitoring the movement of the reaction zone through the catalyst bed. The effluent from reactor 10 is then fed to condenser 22 and the alkylated aromatic product is recovered.

In the experimental work carried out in accordance with the present invention, four steam modified beta catalyst were employed both in the gas and liquid phase alkylation of benzene with ethylene to produce ethylbenzene. For comparative purposes, a beta catalyst which was not subjected to steam treatment was also utilized, again under both liquid and vapor phase conditions.

Catalyst Preparation

A parent, or "as synthesized," beta zeolite was ion-exchanged with ammonium ions in an aqueous solution of ammonium nitrate (in excess of zeolite by weight) at approximately 90° C. for 4 hours. This sample was then filtered, washed and dried at 110° C. for at least 6 hours, and subsequently calcined at 550° C. for 2 to 3 hours. The calcined sample was then dealuminated by high temperature steamings (between 550° C. and 700° C.) for approximately 2 hours. The dealuminated samples were then subjected to two successive ion-exchanges differing from the earlier exchanges in that proton ions were exchanged under acidic conditions in the latter exchanges. Each of the beta zeolite samples was then extruded with 20% alumina as binder and calcined at a maximum temperature of 530° C. for 2 hours.

Listed below in Table I is a tabulation of the steam modified beta zeolites tested, indicating steaming temperature, surface area of the powder sample prior to extrusion with 20% alumina binder, surface area of the final extrudate, and the $SiO_2/Al_2O_3$ molar ratio of the catalyst before extrusion.

TABLE I

| Steaming Temp., °C. | Surface Area (m$^2$/g) Powder | Surface Area (m$^2$/g) Extr. | $SiO_2/Al_2O_3$ Molar Ratio |
|---|---|---|---|
| None | 750.0 | 609.1 | 30.9 |
| 600 | 602.4 | 542.0 | 227.3 |
| 650 | 586.4 | 541.0 | 209.7 |
| 550 | 631.9 | 564.1 | 214.2 |
| 700 | 559.5 | 517.6 | 349.2 |

Gas and Liquid Phase Alkylation

Each of the foregoing steam modified beta zeolites was utilized in the gas and liquid phase alkylation of benzene with ethylene to produce ethylbenzene. For comparative purposes, the unmodified beta zeolite was also employed under gas and liquid phase conditions. The reaction conditions are listed below:

|  | Gas Phase | Liquid Phase |
|---|---|---|
| Reactor Mode: | Down-flow | Up-flow |
| Pressure (psig): | 300 | 600 |
| Benzene Feed, LHSV (hr.−1): | approx. 12 | approx. 12 |
| Ethylene Feed: | 30 Mole % in Nitrogen | 30 mole % in Nitrogen |
| Ethylene/Benzene Mole Ratio: | approx. 8 | approx. 8 |
| Temperature (°C.): | 300–400 | 200 |

Listed below in Tables II and III are summaries of the results obtained for gas and liquid phase ethylbenzene production, respectively.

TABLE II (Vapor Phase Alkylation Results)

| Hβ (no steaming) | | | | | | |
|---|---|---|---|---|---|---|
| Temperature (°C.) | 300 | 300 | 300 | 325 | 350 | 375 |
| Time-on-stream, (hr) | 1.5 | 2.5 | 27 | 50 | 75.5 | 99 |
| % Ethylene Conv. | 99.37 | 99.37 | 99.46 | 99.93 | 99.91 | 99.76 |
| % Benzene Conv. | 15.45 | 15.42 | 15.47 | 15.35 | 15.26 | 15.29 |
| EB Yield, wt. % | 13.93 | 13.90 | 13.98 | 13.74 | 13.42 | 13.17 |
| % Molar Sel: EB | 89.73 | 89.77 | 89.96 | 89.14 | 87.57 | 85.78 |
| DEB | 4.20 | 4.33 | 5.60 | 5.27 | 4.70 | 4.44 |
| EB + DEB | 93.93 | 94.10 | 95.56 | 94.40 | 92.27 | 90.23 |
| Xylenes | 0.017 | 0.018 | 0.004 | 0.012 | 0.031 | 0.053 |
| Hβ (steamed at 550° C.) | | | | | | |
| Temperature (°C.) | 350 | 350 | 350 | 350 | | |
| Time-on-stream, (hr) | 1 | 2 | 26.5 | 51.5 | | |
| % Ethylene Conv. | 93.85 | 93.85 | 91.34 | 90.74 | | |
| % Benzene Conv. | 16.04 | 15.82 | 16.06 | 16.29 | | |
| EB Yield, wt. % | 14.00 | 13.81 | 13.84 | 14.05 | | |
| % Molar Sel: EB | 87.01 | 87.01 | 85.94 | 85.94 | | |
| DEB | 7.37 | 7.80 | 8.91 | 9.06 | | |
| EB + DEB | 94.38 | 94.81 | 94.85 | 95.00 | | |
| Xylenes | 0.019 | 0.018 | 0.016 | 0.015 | | |
| Hβ (steamed at 600° C.) | | | | | | |
| Temperature (°C.) | 400 | 400 | 400 | 400 | 400 | |
| Time-on-stream, (hr) | 1 | 2 | 25 | 47.5 | 72.5 | |
| % Ethylene Conv. | 98.4 | 98.4 | 98.5 | 97.9 | 96.7 | |
| % Benzene Conv. | 17.7 | 17.6 | 17.5 | 17.7 | 16.3 | |
| EB Yield, wt. % | 13.64 | 13.91 | 14.43 | 14.71 | 13.65 | |
| % Molar Sel: EB | 77.45 | 79.44 | 83.09 | 84.25 | 85.80 | |
| DEB | 2.84 | 3.06 | 3.79 | 4.14 | 9.01 | |
| EB + DEB | 80.29 | 82.50 | 86.88 | 88.39 | 94.81 | |
| Xylenes | 0.22 | 0.17 | 0.10 | 0.08 | 0.03 | |
| Hβ (steamed at 650° C.) | | | | | | |
| Temperature (°C.) | 350 | 350 | 350 | 350 | 350 | 350 |
| Time-on-stream, (hr) | 1 | 2 | 25.75 | 48.5 | 71.5 | 95.5 |
| % Ethylene Conv. | 99.8 | 99.96 | 99.99 | 99.08 | 98.80 | 98.06 |
| % Benzene Conv. | 15.84 | 15.88 | 15.66 | 15.71 | 15.49 | 15.48 |
| EB Yield, wt. % | 13.87 | 13.89 | 13.51 | 13.46 | 13.32 | 13.24 |
| % Molar Sel: EB | 87.24 | 87.14 | 86.00 | 85.35 | 85.67 | 85.21 |
| DEB | 7.77 | 7.94 | 9.01 | 9.35 | 9.45 | 9.84 |
| EB + DEB | 95.01 | 95.07 | 95.01 | 94.70 | 95.12 | 95.05 |
| Xylenes | 0.015 | 0.015 | 0.013 | 0.013 | 0.012 | 0.011 |
| Hβ (steamed at 700° C.) | | | | | | |
| Temperature (°C.) | 350 | 350 | 375 | 400 | 400 | 400 |

TABLE II-continued (Vapor Phase Alkylation Results)

| Time-on-stream, (hr) | 1 | 2 | 21.5 | 45.5 | 72 | 93.45 |
|---|---|---|---|---|---|---|
| % Ethylene Conv. | 48.9 | 48.9 | 98.00 | 97.92 | 57.38 | 45.48 |
| % Benzene Conv. | 11.62 | 11.26 | 11.65 | 12.46 | 11.68 | 10.54 |
| EB Yield, wt. % | 9.79 | 9.54 | 9.86 | 10.56 | 9.95 | 9.06 |
| % Molar Sel: EB | 83.81 | 84.27 | 84.22 | 84.36 | 84.82 | 85.50 |
| DEB | 12.09 | 11.81 | 11.89 | 12.00 | 11.75 | 10.96 |
| EB + DEB | 95.90 | 96.08 | 96.11 | 96.36 | 96.40 | 96.46 |
| Xylenes | 0 | 0 | 0 | 0 | 0.005 | 0 |

TABLE III (Liquid Phase Alkylation)

| H$\beta$ (no steam) | | | | | |
|---|---|---|---|---|---|
| Time-on-stream, (hr) | 1 | 2 | 27.5 | 51 | 70 |
| EB Yield, Wt. % | 15.23 | 15.11 | 14.49 | 14.04 | 13.93 |
| DEB Yield, wt. % (Rel. to EB) | 7.04 | 6.98 | 6.49 | 6.36 | 6.33 |
| m-DEB | 4.31 | 4.26 | 3.81 | 3.70 | 3.65 |
| p-DEB | 2.03 | 2.01 | 1.86 | 1.82 | 1.82 |
| o-DEB | 0.70 | 0.71 | 0.82 | 0.84 | 0.86 |
| Xylene Yield, ppm (Rel. to EB) | 0 | 0 | 0 | 0 | 0 |
| H$\beta$ (steamed at 550° C.) | | | | | |
| Time-on-stream, (hr) | 1 | 2 | 27 | 52.5 | 70.5 |
| EB Yield, Wt. % | 9.55 | 9.38 | 7.84 | 6.06 | 6.46 |
| DEB Yield, wt. % (Rel. to EB) | 6.62 | 6.53 | 5.86 | 4.54 | 4.89 |
| m-DEB | 2.29 | 2.24 | 1.99 | 1.54 | 1.66 |
| p-DEB | 2.22 | 2.20 | 2.05 | 1.63 | 1.74 |
| o-DEB | 2.11 | 2.09 | 1.82 | 1.37 | 1.49 |
| Xylene Yield, ppm (Rel. to EB) | 0 | 0 | 0 | 0 | 0 |
| H$\beta$ (steamed at 600° C.) | | | | | |
| Time-on-stream, (hr) | 1 | 2 | 27 | 47 | 69 |
| EB Yield, Wt. % | 10.11 | 9.99 | 9.37 | 8.61 | 9.34 |
| DEB Yield, wt. % (Rel. to EB) | 6.62 | 6.52 | 6.24 | 5.84 | 6.81 |
| m-DEB | 2.37 | 2.32 | 2.17 | 2.01 | 2.33 |
| p-DEB | 2.16 | 2.14 | 2.09 | 1.98 | 2.33 |
| o-DEB | 2.09 | 2.06 | 1.98 | 1.85 | 2.15 |
| Xylene Yield, ppm (Rel. to EB) | 0 | 0 | 0 | 0 | 0 |
| H$\beta$ (steamed at 650° C.) | | | | | |
| Time-on-stream, (hr) | 0.5 | 1 | 24.5 | 49 | 67.75 |
| EB Yield, Wt. % | 6.11 | 4.35 | 5.51 | 7.07 | 5.17 |
| DEB Yield, wt. % (Rel. to EB) | 5.68 | 3.28 | 4.01 | 6.34 | 3.87 |
| m-DEB | 1.92 | 1.11 | 1.36 | 2.16 | 1.31 |
| p-DEB | 2.02 | 1.16 | 1.40 | 2.21 | 1.36 |
| o-DEB | 1.74 | 1.01 | 1.25 | 1.97 | 1.20 |
| Xylene Yield, ppm (Rel. to EB) | 0 | 0 | 0 | 0 | 0 |

Examination of the experimental data presented in Table II indicates that all of the beta zeolites utilized are quite active for the production of ethylbenzene under vapor phase conditions. The steam modified beta catalysts exhibited good stability, high conversions and very low xylene selectivity. Total molar selectivities toward mono- and di-alkylation exceeded 95% in some cases, with a reduction in xylene formation below that of the unmodified beta catalyst.

The data in Table III indicates that the steam modified catalysts are less active for ethylbenzene production than the unmodified beta catalyst under liquid phase conditions. Virtually no xylenes were produced using any of the catalysts. An interesting phenomenon occurring only in the liquid phase runs was the essentially stoichiometric distribution of meta, para, and ortho diethylbenzene isomers obtained with the modified catalyst as compared to the expected thermodynamic equilibrium distribution resulting from use of the unmodified catalyst.

Having described specific embodiments of the present invention, it will be understood that modification thereof may be suggested to those skilled in the art, and it is intended to cover all such modifications as fall within the scope of the appended claims.

We claim:

1. A process for the production of ethylbenzene, comprising:
   (a) Supplying a feedstock containing benzene into a reaction zone and into contact with a zeolite beta alkylation catalyst which has been modified by steaming at a temperature between about 550° C. and 750° C. and has a silica to alumina mole ratio in excess of 50;
   (b) Supplying an ethylating agent to the reaction zone;
   (c) Operating the reaction zone at alkylation reaction conditions effective to ethylation of the benzene in the presence of the alkylation catalyst;
   (d) Recovering the ethylbenzene from the reaction zone.

2. The process as recited in claim 1 wherein the zeolite beam alkylation catalyst has a silica to alumina mole ratio between about 70 and 200.

3. The process as recited in claim 2 wherein the alkylation reaction conditions include a temperature and pressure sufficient to maintain essentially vapor phase alkylation conditions.

4. The process as recited in claim 3 wherein the alkylation reaction conditions include a temperature between about 270° and 400° C., a pressure between about 200 to 600 psig, a liquid hourly space velocity between about 10 and 70 hour$^{-1}$, and a benzene:ethylating agent molar ratio between about 3 and 20.

5. The process as recited in claim 2 wherein the alkylation reaction conditions include a temperature and pressure sufficient to maintain essentially liquid phase alkylation conditions.

6. The process as recited in claim 5 wherein the alkylation reaction conditions include a temperature between about 38° and 300° C., a pressure between about 200 and 600 psig, a liquid hourly space velocity between about 10 and 70 hour$^{-1}$, and an aromatic substrate:alkylating agent molar ratio between about 3 and 20.

7. The process as recited in claim 2 wherein the ethylating agent is diluted with a diluting agent prior to contact with the benzene, the diluting agent being nondeleterious to the alkylation reaction or alkylation catalyst.

8. The process as recited in claim 7 wherein the diluting agent is nitrogen.

9. The process as recited in claim 3 wherein the aromatic substrate is benzene and the ethylating agent is ethylene.

10. The process as recited in claim 5 wherein the ethylating agent is ethylene.

11. The process as recited in claim 9 wherein the mole percent selectivity toward ethylbenzene and diethylbenzene is greater than 90%.

12. The process as recited in claim 9 wherein the mole percent selectivity toward xylene is less than 0.03%.

13. The process as recited in claim 10 wherein the xylene yield relative to ethylbenzene production is less than 50 ppm.

14. The process as recited in claim 10 wherein the distribution of meta, para, and ortho diethylbenzene isomers produced is essentially stoichiometric.

* * * * *